United States Patent [19]

Martinez et al.

[11] 4,327,233

[45] Apr. 27, 1982

[54] METHOD FOR PRODUCING CARBOCYCLIC COMPOUNDS FROM CYCLIC SULFIDE

[75] Inventors: Richard I. Martinez, Gaithersburg; John T. Herron, Darnestown, both of Md.

[73] Assignee: The United States of America as represented by the Secretary of Commerce, Washington, D.C.

[21] Appl. No.: 247,684

[22] Filed: Mar. 26, 1981

[51] Int. Cl.³ .............................................. C07C 1/00
[52] U.S. Cl. .................................. 585/357; 585/371; 585/317
[58] Field of Search ............................... 585/371, 357

[56] References Cited

U.S. PATENT DOCUMENTS 2,414,880  1/1947  Kistiakowsky et al. ........ 204/162 R
2,753,380  7/1956  Pines et al. ......................... 585/317

OTHER PUBLICATIONS

Conner et al., Tetrahedron Lett., 1967, 4925–4929.
R. L. Martinez and J. T. Herron, Chem. Phys. Lett., 72, 74, (1980).
F. H. Dover and K. E. Salomon, J. Phys. Chem., 84, 1302, (1980).
Chemical Abstracts, 62, 2752c, 93, 237998q, 83, 114130m.

*Primary Examiner*—Thomas A. Waltz
*Assistant Examiner*—A. Pal
*Attorney, Agent, or Firm*—Eugene J. Pawlikowski; Alvin J. Englert

[57] ABSTRACT

A method is provided for producing a carbocyclic compound by contacting an organic compound containing a 4–8 membered cyclic sulfide with ozone, in the vapor phase, and recovering a product containing a 3–7 membered carbocyclic ring.

18 Claims, 1 Drawing Figure

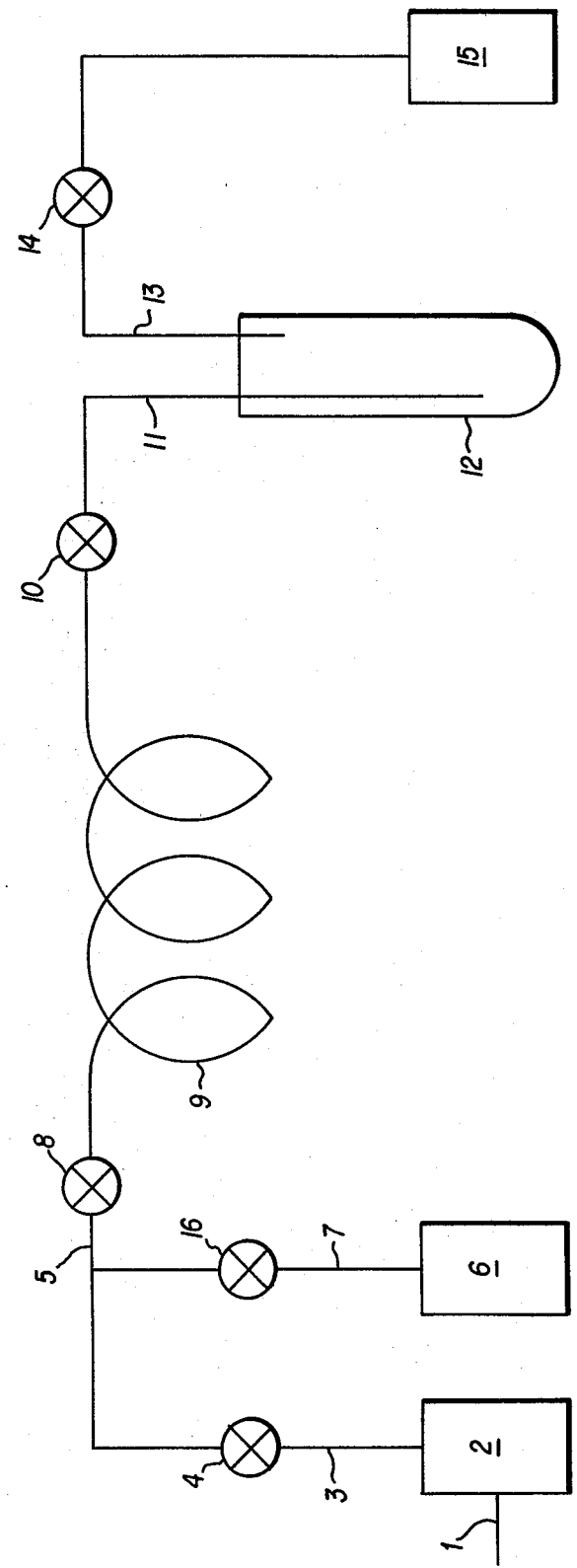

METHOD FOR PRODUCING CARBOCYCLIC COMPOUNDS FROM CYCLIC SULFIDE

BACKGROUND OF THE INVENTION

This invention relates to a method for producing a carbocyclic compound by extrusion of a sulfur atom from a cyclic sulfide.

Carbocyclic compounds are produced by a variety of synthetic pathways. Many examples are known of carbocyclic ring contraction reactions, wherein a carbon atom which is part of a ring is extruded, to produce a smaller carbocyclic ring containing one or more fewer carbon atoms. Such reactions are summarized by Redmore et al., in *Advances in Alicyclic Chemistry,* Hart et al., Eds., Vol. 3, 1-138 (Academic Press, 1971). It is known that when α-halo sulfones are treated with base, olefins are produced, with extrusion of sulfur dioxide. A reductive extrusion of sulfur from episulfides to form olefins is also known. However, extrusion of sulfur in a single step from a cyclic sulfide, to produce a carbocyclic ring having a carbon-carbon single bond linking those carbons formerly joined to sulfur, is unprecedented.

The method of the present invention is particularly suitable for the production of substituted or unsubstituted cyclobutanes. Known methods for synthesizing cyclobutanes include the condensation of 1,3-dibromopropanes with malonic ester or other activated methylene, dimerization of ketenes, allenes, acrylonitrile and polyfluoroethylenes. In addition, photoaddition of olefins to unsaturated ketones has been used to build a cyclobutane ring onto a conjugated double bond.

Cyclobutane itself may be produced from the malonic ester condensation product by decarboxylation, reduction to cyclobutylmethanol and catalytic dehydroxymethylation, as taught in U.S. Pat. No. 2,753,380 to Pines et al. Alternatively, the photolysis of cyclopentanone produces a minor percentage of cyclobutane and a major percentage of ethylene, as taught in U.S. Pat. No. 2,414,880 to Kistiakowsky et al. 1,4-dibromobutane has been coupled with lithium amalgam to give cyclobutane, by Connor et al., *Tet. Let,* 1967, 4925.

The present inventors investigated the reaction of ozone and thiirane, and found that this system rapidly converts to an ozone-olefin-SO₂ system. Furthermore, the ethylene then reacts with the ozone to produce other radicals, especially OH radicals, which are the principal chain carriers of the reaction, as reported in *Chem. Phys. Let.,* 72, 74 (1980). The authors suggested that analogous results might be anticipated for the reaction of ozone with the homologous episulfides and possibly also for higher cyclic sulfides. Finally, Dorer et al., *J. Phys. Chem.,* 84, 1302 (1980), reported a study of the gas phase photolysis of tetramethylene sulfoxide. The photolysis was affected at various excitation wavelengths, including mercury sensitization, and a variety of products were observed, including cyclobutane, although cyclobutane was never the exclusive product. The authors maintain consistently that cyclobutane is produced through a tetramethylene diradical, a position which also requires that ethylene be produced concomitantly.

There is no suggestion in the combined teachings of the prior art references that a non-photolytic process could convert a cyclic sulfide to a carbocyclic compound with extrusion of sulfur, where the carbocyclic ring is substantially the exclusive product, and where substantially no olefin is formed. Moreover, in the case of cyclobutane, the intermediacy of a tetramethylene diradical was uniformly considered to be involved in any reaction wherein a cyclic ketone or sulfur-containing precursor is reacted to eliminate sulfur and to produce hydrocarbon products, so that olefinic products were always expected as well.

Cyclobutane is useful as a detection compound in actinometry, the measurement of light intensity, in the vacuum ultraviolet region, in liquid phase. It forms ethylene with a quantum yield of 2. Furthermore, compounds containing cyclobutane rings have been shown to be useful in applications as diverse as pharmaceuticals, e.g., cyclobutane analogs of prostanoids, anesthetics, progestational agents, antipyretics, antihypertensives, and in perfume and dentifrice preparations. The method of the invention is also useful in providing an alternative pathway to fused, bridged and/or spirocyclic ring systems of interest to both synthetic chemists and theoreticians.

A need therefore continues to exist for a simple and practical method of producing carbocyclic compounds, especially compounds containing a cyclobutane ring.

OBJECTS OF THE INVENTION

One object of the present invention is to provide a method for producing a carbocyclic compound from a precursor containing a 4-8 membered cyclic sulfide, in a single step.

Another object of the present invention is to provide a method for producing substituted or unsubstituted cyclobutanes, by a process which avoids the lengthy synthetic pathways and other attendant disadvantages of prior art methods.

A further object of the invention is to provide a simple, inexpensive and efficient synthesis of cyclobutane from a readily available commercial precursor.

Upon further study of the specification and appended claims, further objects and advantages of this invention will become apparent to those skilled in the art.

SUMMARY OF THE INVENTION

The foregoing objects are achieved by providing a method for producing a carboxylic compound, which comprises contacting an organic compound containing a 4-8 membered cyclic sulfide and having the formula $$A \underset{}{\bigcirc} S,$$

wherein A is an alkyl-substituted or unsubstituted divalent 3-7 carbon alkylene bridge, with ozone, in the vapor phase, and recovering from the resultant reaction mixture a product containing a 3-7 membered carbocyclic ring and having the formula A , wherein A is as defined hereinabove; wherein substantially no non-sulfur-containing compound having olefinic unsaturation instead of said 3-7 membered carbocyclic ring is produced in said reaction mixture.

BRIEF DESCRIPTION OF THE DRAWING

The FIGURE is a schematic of a process according to the invention.

DETAILED DISCUSSION

The present invention provides a general method for transforming a compound having a 4-8 membered cyclic sulfide ring as a part of the molecule into the corresponding compound having a 3–7 membered carbocyclic ring in place of the cyclic sulfide, by extrusion of the sulfur in a single step, in the vapor phase, under the action of ozone.

The starting material for the process of the invention is most generally represented by the formula

wherein A is a moiety containing a divalent 3–7 carbon alkylene bridge whose two termini are joined to a sulfur atom to form a 4–8 membered cyclic sulfide moiety. The product of the reaction is formed by extrusion of the sulfur atom with concommitant joining of the two termini of the bridge through a single bond to form a 3–7 membered carbocyclic ring, represented as A⟩ . That is, the two carbon atoms at each end of the bridge that are each joined by single bonds to the sulfur atom in the starting compound end up joined to one another by a single carbon-carbon bond in the product.

The 4–8 membered cyclic sulfide moiety may be part of a variety of molecular structures. For example, the cyclic sulfide may be part of a fused ring system, a bridged bicyclic or polycyclic ring system, and/or a spirocyclic ring system, in which case the product will have a fused, bridged and/or spirocyclic carbocyclic ring. Such compounds may be generally represented by the formula

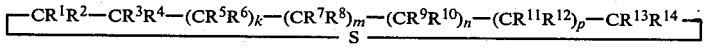

wherein each of $R^1$–$R^{14}$ independently is H or $C_{1-6}$ alkyl, or any two or more of $R^1$–$R^{14}$ form an alkyl-substituted or unsubstituted fused, bridged or spirocyclic ring; and k, m, n and p are each independently 0 or 1. The fused ring system, 2-thioperhydroindene, compound 6 in Table I below, is represented by the above formula, wherein $R^1=R^2=R^3=R^5=R^{13}=R^{14}=H$; $R^4$ and $R^6$ together are a tetramethylene bridge; k=1; and m=n=p=0. The bridged bicyclic compound, 2-thiabicyclo[2.2.2]octane, compound 4 in Table I below, is represented by the above formula, wherein $R^1=R^2=R^3=R^5=R^6=R^7=R^8=R^{13}=H$; $R^4$ and $R^{14}$ together are an ethylene bridge; k=m=1; and n=p=0. The spirocyclic sulfide, 2-thiaspiro[4.4]nonane, compound 5 in Table I below, is represented by the above formula, wherein $R^1=R^2=R^5=R^6=R^{13}=R^{14}=H$; $R^3$ and $R^4$ together are a tetramethylene bridge; k=1; and m=n=p=0.

The bridge moiety may be simply a substituted or unsubstituted carbon chain, e.g., trimethylene, tetramethylene, pentamethylene, hexamethylene or heptamethylene, in which case the carbocyclic product would be cyclopropane, cyclobutane, cyclopentane, cyclohexane, or cycloheptane, respectively, with the same substituents that were present in the cyclic sulfide precursor. Cyclic sulfides of this type are conveniently represented by the formula

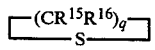

wherein $R^{15}$ and $R^{16}$ are each independently H or alkyl, preferably $C_{1-6}$ alkyl; and q is an integer of from 3 to 7.

Substituents on the cyclic sulfide-containing starting material may include any group or atom which is inert to ozone and which does not interfere with the reaction. Preferably, such substituents are alkyl groups, most preferably $C_{1-6}$ alkyl groups, or hydrogen atoms. While it is conceivable that certain substituents on the two termini of the alkylene bridge, i.e., the carbon atoms linked to sulfur, may make competing reaction pathways energetically accessible and divert the reaction from the pathway leading to carbocyclic products, this is unlikely in view of the present disclosure. Conversely substituents more than two carbon atoms removed from the termini of the alkylene bridge will normally have a minimal effect on the course of the reaction.

Examples of structures illustrative but not limitative of the scope of the cyclic sulfide reactants are shown in Table I.

TABLE I

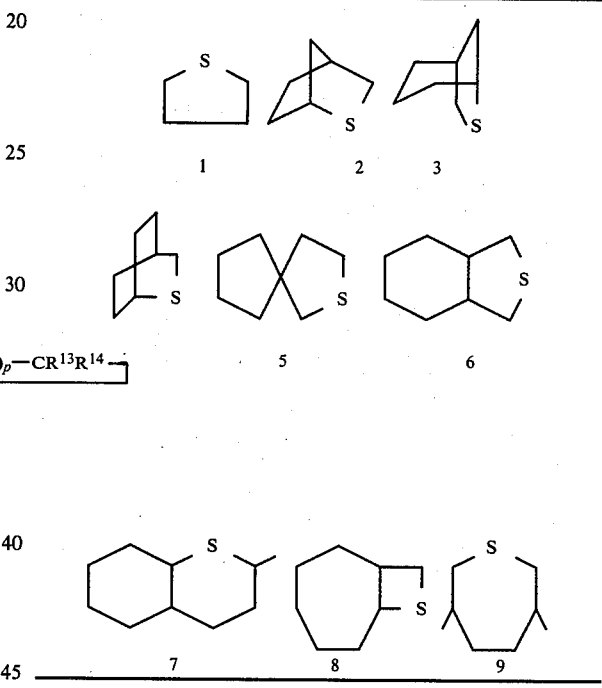

The method of the invention is particularly well adapted to producing cyclobutane from the readily available thiolane. While the prior art reactions leading to cyclobutane by way of photolysis of either cyclopentanone or tetramethylene sulfoxide both proceed through the tetramethylene diradical, this is apparently not the case when cyclobutane is produced by the present method. The tetramethylene diradical can cyclize to cyclobutane or fragment into two molecules of ethylene. Both of the prior art photolytic processes produced substantial amounts of ethylene along with any cyclobutane produced. Surprisingly and unexpectedly, the present process produces cyclobutane but substantially no ethylene or other olefins such as 1-butene, which Dorer et al found to be a photolysis product of tetramethylene sulfoxide.

While not wishing to be bound by any particular mechanism, the failure to detect significant amounts of ethylene, as well as the excellent correlation between the rate of disappearance of thiolane and the rate of appearance of cyclobutane, strongly support a mechanism such as that of Scheme I.

SCHEME I

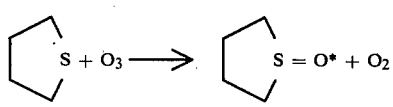 (1)

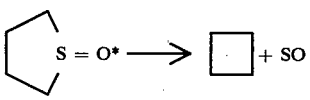 (2)

 (3)

According to this mechanism, thiolane reacts with ozone to form a vibronically excited sulfoxide, which decomposes in a concerted unimolecular fashion to form cyclobutane and sulfur monoxide, the latter reacting with ozone to form sulfur dioxide. This mechanism is consistent with thermochemical calculations on this system. Furthermore, no excited-neutral-metastable sulfur dioxide is formed, contrary to the expectation if significant quantities of ethylene or other olefin had been formed.

It appears that the unexpected and surprising unimolecular extrusion of sulfur monoxide from the vibronically excited sulfoxide intermediate produced by chemical reaction is responsible for the fact that the present reaction cleanly produces carbocyclic products rather than ring cleavage products, which would be expected if diradical intermediates intervened. Accordingly, the present reaction affords a general method of producing carbocyclic compounds from cyclic sulfide precursors. Moreover, the present process is unexpectedly superior to photolytic or mercury-sensitized processes for fragmenting cyclic ketones or sulfoxides, since these photolytic processes involve alkylene diradicals which produce alkenes, and other byproducts, in addition to carbocyclic products.

Cyclic sulfides suitable for use in the present process may be prepared by a variety of conventional methods. A representative selection of such synthetic pathways are shown in Scheme II.

SCHEME II

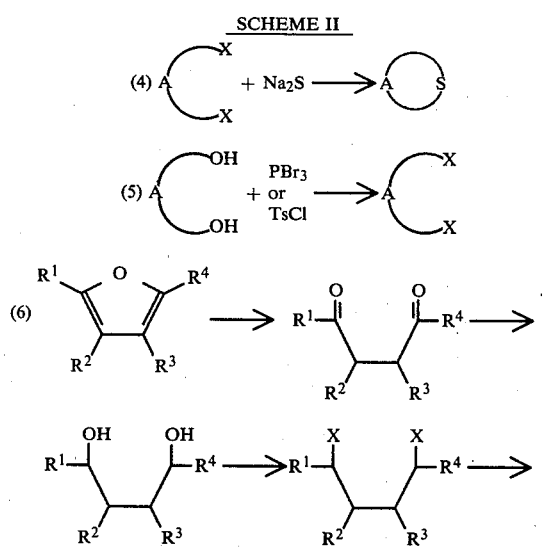

-continued
SCHEME II

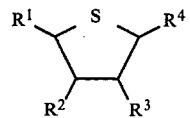

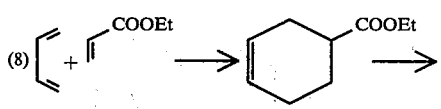 (7)

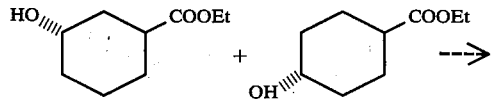

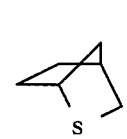

2

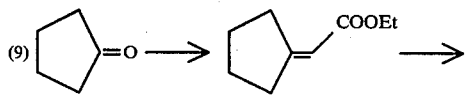 (8)

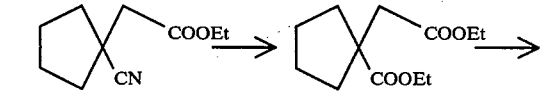

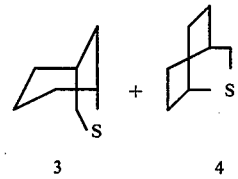

3    4

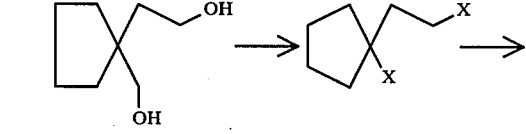 (9)

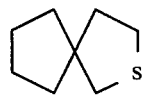

5

-continued
SCHEME II

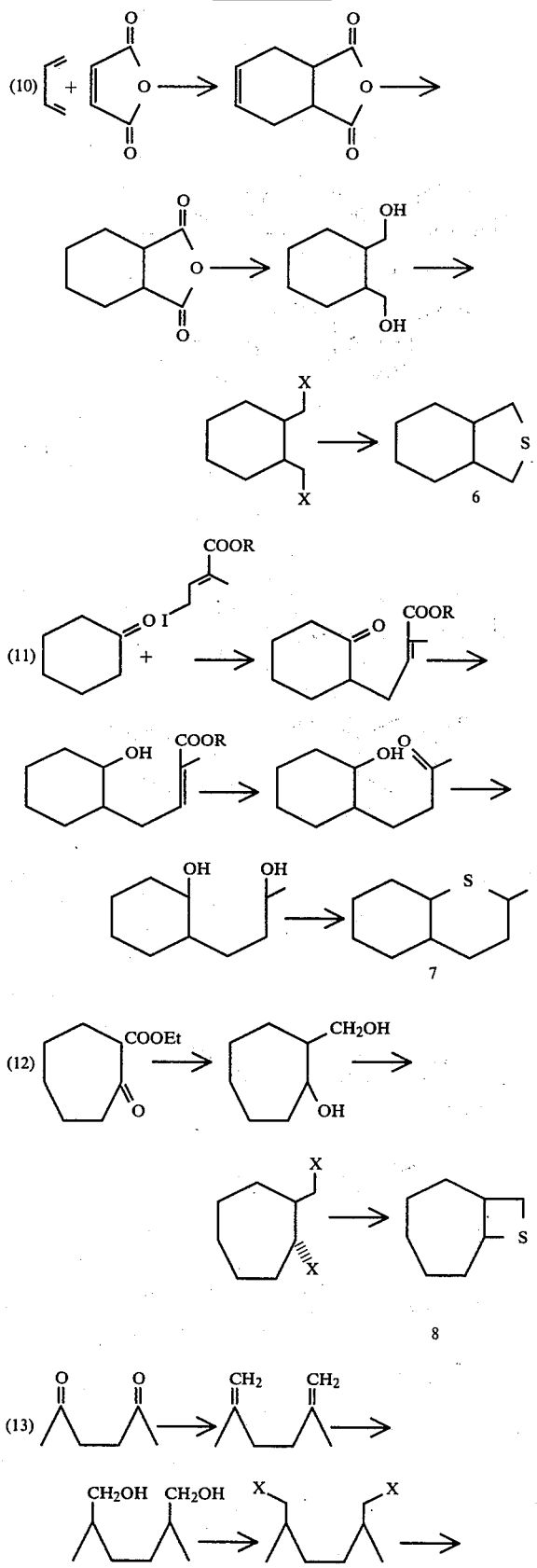

-continued
SCHEME II

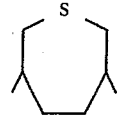

9

Those simple cyclic sulfides which are not available commercially may be synthesized by reacting dihalides or bis-sulphonates, e.g., bis-toluenesulphonates (tosylates), with sodium sulfide, as shown in reaction (4), wherein X is a halide, e.g., Cl, Br or I, or a tosylate. The halides and/or tosylates may be formed from the corresponding diols, as shown in reaction (5).

1,4-diols are conveniently prepared by reduction, e.g., with $NaBH_4$, of 1,4-diketones, which in turn are conveniently prepared by, e.g., acid-catalyzed hydrolysis of furans, as shown in reaction (6). The 1,4-diols are converted to dihalides or bis-tosylates, which in turn are cyclized with sodium sulfide.

Bridged bicyclic sulfides such as compounds 2, 3 and 4 may conveniently be prepared from monocyclic precursors. For example, as shown in reaction (7), the known 3-cyclopentenyl tosylate (Allred et al., *J. Am. Chem. Soc.*, 81, 5833 (1959); *J. Org. Chem.*, 25, 26 (1960)) is converted, by displacement of the tosylate by cyanide, hydrolysis and esterification, hydroboration-/oxidation of the double bond to form an alcohol, reduction of the ester to a primary alcohol, conversion of the alcohols to tosylates, and reaction of the bis-tosylate with sodium sulfide, to 2-thiabicyclo[2.2.1]heptane, compound 2.

Reaction (8) illustrates the formation of related bridged bicyclic compounds. Thus, the Diels-Alder adduct of butadiene and ethyl acrylate may be converted to a mixture of alcohols by hydroboration/oxidation, each of which may be further transformed analogously to the sequence of reaction (7) to bridged bicyclic cyclic sulfides, 5-thiabicyclo[3.2.1]octane, compound 3, and 2-thiabicyclo[2.2.2]octane, compound 4, respectively.

Spirocyclic compounds containing a 5-membered cyclic sulfide ring may be prepared by reaction (9). Cyclopentanone is converted to an exocyclic unsaturated ester, either by the Emmons modification of the Wittig reaction using a phosphonoacetate anion, or by a Reformatsky reaction using zinc and ethyl bromoacetate, followed by dehydration. Cyanide addition to the unsaturated ester, followed by hydrolysis and esterification, produces a diester, which may be reduced with, e.g., lithium aluminum hydride, to a diol, which is converted to, e.g., a dihalide, and cyclized with sodium sulfide to form 2-thiaspiro[4.4]nonane, compound 5.

The Diels-Alder adduct of butadiene and maleic anhydride, may be catalytically hydrogenated and reduced with lithium aluminum hydride to form a diol which, after conversion to a dihalide and cyclization with sodium disulfide, produces 2-thiaperhydroindene, compound 6, using the sequence of reaction (10).

Fused ring cyclic sulfides, such as 2-methyl-1-thiaperhydronaphthalene, compound 7, may be produced by means of a sequence such as reaction (11). Cyclohexanone is alkylated, e.g., through its enamine or its enolate, with t-butyl 4-iodotiglate, to form a ketoester, which is reduced to a hydroxyester with, e.g., sodium borohydride. The ester is hydrolyzed, converted to an acyl azide, and the acyl azide is converted by a Curtius rearrangement to a vinyl isocyanate, which is hydrolyzed to a ketone. The foregoing steps are part of a sequence reported by Stotter et al., *J. Am. Chem. Soc.*, 96, 6524 (1974). The ketone is reduced to an alcohol, and the diol is converted by way of a dihalide or bis-tosylate to the cyclic sulfide of compound 7 by reaction with sodium sulfide.

A fused ring cyclic sulfide having a 4-membered ring may be produced by a reaction sequence such as that of reaction (12). The ketoester resulting from Claisen condensation of diethyl carbonate with cycloheptanone is reduced to a diol, converted to a dihalide or bis-tosylate, and cyclized with sodium sulfide to form 7-thiabicyclo[5.2.0]nonane, compound 8.

An example of a 7-membered cyclic sulfide having substituents at C3 and C6 may be prepared by a sequence such as that of reaction (13). A 1,4-diketone analogous to the diketone intermediate in reaction (6), wherein $R^1$ and $R^4$ are $CH_3$ and $R^2$ and $R^3$ are H, is converted to the bis-methylene compound by, e.g., a Wittig reaction with a methylenetriphenylphosphorane. Bis-hydroboration/oxidation produces a diol, which is converted to a dihalide or bis-tosylate, and cyclized with sodium sulfide, to produce 3,6-dimethylthiepane, compound 9.

Other cyclic sulfides suitable for use as starting materials in the present process may be produced by modification or combination of the foregoing illustrative reaction sequences, or by other conventional pathways. The Arndt-Eistert homologation and the malonic ester synthesis are examples of chain-extension reactions which can be used to vary the length of an ester-containing chain in any of the above reactions to form larger rings after eventual reduction of the ester function. Similarly, various chain-contraction reactions such as the Hoffman rearrangement may be used to remove a carbon atom from a chain to eventually produce a smaller cyclic sulfide ring. Thus, the reactions of Scheme II may be further extended in each case to form compounds having smaller or larger cyclic sulfide rings in the various configurations illustrated. Similarly, conventional reactions are known to produce, e.g., alkyl-substituted starting materials for the sequences of Scheme II, so that alkyl-substituted analogs of the various cyclic sulfides shown are also available.

The method of the invention is effected in the vapor phase. Ozone and the cyclic sulfide are mixed in a reaction vessel or in a continuous reaction system. The ozone may be supplied as a mixture of ozone and oxygen, as it is produced by a conventional ozone generator. The ozone generator advantageously produces ozone in a concentration of about 3–10% $O_3$ in $O_2$. Pure ozone may also be used.

The cyclic sulfide is vaporized by any conventional means. The gaseous cyclic sulfide is mixed with the ozone in such a fashion as to ensure efficient mixing, e.g., by use of a radial mixing device, an impeller, or the like. The ratio of the partial pressure of ozone to the partial pressure of the cyclic sulfide, which will also be the molar ratio, advantageously ranges from 0.5 to 20, preferably from 2 to 10. The cyclic sulfide may be mixed with an inert diluent, such as argon.

The total pressure of ozone, cyclic sulfide, and any oxygen or optional diluent is limited only by the requirement that the pressure not be so high as to appreciably quench the intermediate excited sulfoxide before it can decompose to the carbocyclic product and sulfur monoxide. The maximum total pressure may be readily determined by analyzing the yield of cyclobutane as a function of pressure, and determining at what pressure the yield of cyclobutane diminishes when the pressure is increased. Advantageously, the total pressure of reactants is from 0.1 to 100 Torr., preferably from 1 to 10 Torr.

The reaction may be effected at room temperature, but may also be effected at lower or higher temperatures. Room temperature, i.e., 12°–30° C., preferably about 20° C., is convenient, since it avoids the need for unnecessary expenditure of energy in cooling or heating the reaction system. A temperature range of from 0° to 125° C. is preferred to either higher or lower temperatures.

The products of the reaction are recovered in a conventional fashion. The method of separation will depend on the volatility of the carbocyclic product. In a large majority of cases, distillation will be the most convenient separation method. The distillation may be effected at atmospheric pressure, at superatmospheric pressure, in the case of more volatile carbocyclics, or at reduced pressure in the case of higher boiling carbocyclic products. Of course, other separation techniques, e.g., chromatography, solvent extraction, chemical separations, and the like may all be used in appropriate cases. Thus, chromatography will be effective for separating the polar sulfide and sulfoxide reactant and intermediate from the non-polar carbocyclic product. It may be advantageous in certain cases to dissolve the reaction mixture in a low boiling organic solvent and extract the sulfur-containing components with an aqueous metal salt solution containing metal ions capable of chelating sulfides and/or sulfoxides. Salts of, e.g., copper, zinc, cadmium, mercury, and the like may be used for aqueous solvent extraction. The product is recovered by distillation, and optionally purified further. Preparative high performance liquid chromatography may also be used for separation and/or purification of the carbocyclic product.

A significant characteristic of the present process is that it converts a cyclic sulfide to a carbocyclic product with substantially no olefin or olefin-derived products being formed. By substantially no olefin is meant less than 5%, preferably less than 2%, and most preferably no detectable olefin or olefin-derived products. Olefin-derived products are those resulting from ozonolysis of olefins, e.g., formaldehyde, formic acid, and the like.

Without further elaboration, it is believed that one skilled in the art can, using the preceding description, utilize the present invention to its fullest extent. The following illustrative example is therefore not limitative in any way whatsoever of the scope of the invention as disclosed hereinabove.

The invention is illustrated by the preparation of cyclobutane from thiolane, and with reference to the drawing. The process is carried out in an apparatus consisting of an ozonator 2, supplied with a stream of oxygen through line 1, and capable of generating a stream of 5% ozone in oxygen, which is supplied to a tubular reactor 9 through lines 3 and 5 and valves 4 and 8. The effluent passes through valve 10 and line 11 into a cold trap 12, and the volatile gases are evacuated through line 13 and valve 14 by a vacuum pump 15. After the system is flushed with oxygen, and evacuated using the pump 15, ozonator 2 is started up, and the 5% ozone stream is regulated with valves 4 and 14 so that a pressure of 8 Torr. is established in the tubular reactor, and a flow rate is maintained such that the residence time of the stream in the tubular reactor is about 10 seconds.

Thiolane is introduced into heater 6 and warmed to generate thiolane vapor. The vapor is metered into line 5 through line 7 and valve 16 at a rate such that the partial pressure of thiolane in the gas stream passing into the tubular reactor is 100 mTorr. The ratio of ozone to thiolane is 4:1, since 5% ozone in oxygen at 8 Torr. produces a partial pressure of ozone of 400 mTorr. The effluent passing through valve 10 and line 11 is trapped on the walls of the cold trap 12, which is cooled to a temperature of −78° C. with a bath of dry ice/acetone (not shown). The uncondensed gases exit the cold trap through line 13 and valve 14 and pass into the pump 15. The tubular reactor is at room temperature.

The reaction is allowed to proceed until a desired quantity of reaction product mixture is accumulated in the cold trap. At that point, valve 16 is closed, ozonator 2 is turned off, and the remaining reaction gases are swept out of tubular reactor 9 with an oxygen stream. At that point, the system is isolated by closing valves 4, 8, 10 and 14. The material condensed in the cold trap is then subjected to a further batchwise separation. This may be effected by a variety of techniques. Cyclobutane may be distilled out by permitting the contents of flask 12 to warm to room temperature at atmospheric pressure, and trapping the cyclobutane at dry ice/acetone temperature in a second bulb. Further purification of the cyclobutane may be effected by percolation of 0° C. through an alumina column and/or by preparative vapor phase chromatography.

In a small scale reaction to study the foregoing process, no ethylene was detected as a reaction product. Moreover, as noted above, no excited-neutral-metastable sulfur dioxide was detected, showing that substantially no olefin-derived products were formed.

Analogous procedures may be used with similar success by substituting other cyclic sulfides for thiolane and/or by using other disclosed operating conditions and recovery methods for those used in the preceding illustrative example. A continuous process may be effected by substituting a continuous physical and/or chemical fractionation for the batchwise purification process illustrated in the Example.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for producing a carbocyclic compound, which comprises contacting an organic compound containing a 4-8 membered cyclic sulfide moiety and having the formula $$A\!\!\bigcirc\!\!S,$$

wherein A is a moiety containing a divalent 3-7 carbon alkylene bridge whose two termini are joined to a sulfur atom to form said cyclic sulfide moiety, with ozone, in the vapor phase, and recovering from the resultant reaction mixture a product containing a 3-7 membered carbocyclic ring formed by extrusion of said sulfur atom and joining of said two termini through a carbon-carbon single bond; wherein substantially no non-sulfur-containing compound having olefinic unsaturation instead of said 3-7 membered carbocyclic ring is produced in said reaction mixture.

2. The method of claim 1, wherein A is a moiety having the formula $$\left[-CR^1R^2-CR^3R^4-(CR^5R^6)_k-(CR^7R^8)_m-(CR^9R^{10})_n-(CR^{11}R^{12})_p-CR^{13}R^{14}-\right]$$

wherein each of $R^1$-$R^{14}$, independently is H or $C_{1-6}$ alkyl, or any two or more of $R^1$-$R^{14}$ form an alkyl-substituted or unsubstituted fused, bridged or spirocyclic ring; and k,m,n and p are each independently 0 or 1.

3. The method of claim 1, wherein A is $-(CR^{15}R^{16})_q-$, wherein $R^{15}$ and $R^{16}$ are each independently H or $C_{1-6}$ alkyl; and q is an integer of from 3 to 7.

4. The method of claim 1, wherein said divalent alkylene bridge is a 4-carbon bridge.

5. The method of claim 2, wherein K=1 and n=n=p=0.

6. The method of claim 3, wherein q=4.

7. The method of claim 3, wherein $R^{15}=R^{16}=H$.

8. The method of claim 1, wherein said organic compound is thiolane, and said product is cyclobutane; and wherein substantially no ethylene is produced.

9. The method of claim 1, wherein said contacting is effected at a temperature of from 0° to 125° C.

10. The method of claim 9, wherein said temperature is from 12° to 30° C.

11. The method of claim 1, wherein said ozone is supplied as a mixture of from 1 to 10% ozone in oxygen, and the total initial pressure of said cyclic sulfide and said ozone-oxygen mixture is from 0.1 to 100 Torr.

12. The method of claim 11, wherein said total initial pressure is from 1 to 10 Torr.

13. The method of claim 1, wherein the molar ratio of ozone to cyclic sulfide-containing compound in said contacting step is from 0.5 to 20.

14. The method of claim 13, wherein said ratio is from 2 to 10.

15. A method of producing cyclobutane, which comprises contacting thiolane with ozone, in the vapor phase, at a temperature of from 0° to 125° C., and recovering the resultant cyclobutane; wherein said ozone is supplied as a mixture of from 1 to 10% ozone in oxygen, and the total initial pressure of thiolane and said ozone-oxygen mixture is from 0.1 to 100 Torr.; and wherein substantially no ethylene is produced.

16. The method of claim 15, wherein said temperature is from 12° to 30° C.

17. The method of claim 15, wherein said total initial pressure is from 1 to 10 Torr.

18. The method of claim 15, wherein the molar ratio of ozone to cyclic sulfide is from 2 to 10.

* * * * *